United States Patent [19]

Okazaki et al.

[11] Patent Number: 4,473,652

[45] Date of Patent: Sep. 25, 1984

[54] METHOD AND IMMUNOCHEMICAL MEASUREMENT

[75] Inventors: Masaki Okazaki; Nobuhito Masuda; Yoshiro Kumano, all of Kanagawa, Japan

[73] Assignee: Fuji Photo Film Co., Ltd., Kanagawa, Japan

[21] Appl. No.: 506,225

[22] Filed: Jun. 22, 1983

Related U.S. Application Data

[63] Continuation of Ser. No. 298,815, Sep. 2, 1981, abandoned.

[30] Foreign Application Priority Data

Sep. 2, 1980 [JP] Japan ............................. 55-120594
Sep. 2, 1980 [JP] Japan ............................. 55-120595

[51] Int. Cl.³ ........................................... G01N 33/54
[52] U.S. Cl. .................................. 436/536; 430/566; 435/7; 436/538; 436/539; 436/540; 436/541
[58] Field of Search ............... 436/536, 537, 538, 539, 436/540, 541; 435/7

[56] References Cited

U.S. PATENT DOCUMENTS

| | | | |
|---|---|---|---|
| 4,331,444 | 5/1982 | Mihara | 23/230 B |
| 4,337,063 | 6/1982 | Mihara | 23/230 B |
| 4,337,065 | 6/1982 | Hiratsuka | 23/230 B |
| 4,404,289 | 9/1983 | Masuda | 436/538 |
| 4,405,711 | 9/1983 | Masuda | 435/4 |
| 4,414,323 | 11/1983 | Masuda | 435/7 |
| 4,414,325 | 9/1983 | Masuda | 435/7 |
| 4,429,050 | 1/1984 | Yasuda | 436/538 |

*Primary Examiner*—Sidney Marantz
*Attorney, Agent, or Firm*—Sughrue, Mion, Zinn, Macpeak & Seas

[57] ABSTRACT

A method for immunochemical assay of an antigen or antibody by labelling the antigen or antibody with a specific cyanine or merocyanine dye containing a carboxy group followed by effecting an immune reaction and photochemical processing thereof is provided. The amount of the antigen or antibody is measured in term of optical density of developed silver halide which is brought into contact with either the antigen-antibody reaction product or the unreacted material.

This immunochemical assay method gives high detection sensitivity in a simple operation manner.

7 Claims, No Drawings

METHOD AND IMMUNOCHEMICAL MEASUREMENT

This application is a continuation of application Ser. No. 298,815, filed Sept. 2, 1981, abandoned.

BACKGROUND OF THE INVENTION

Field of the Invention

This invention relates to a method for photochemical and immunological measurement of an antigen or antibody, more particularly, to a method for immunochemical assay or measurement of an antigen or antibody by labelling the antigen or antibody with a cyanine or merocyanine dye containing a carboxy-containing substituent followed by effecting an immune reaction and photochemical processing thereof.

DEVELOPMENT OF THE INVENTION

A method for photochemical measurement of a trace component which comprises labelling an antigen or antibody with a spectral sensitizer instead of a radioisotope or an enzyme, subjecting the labelled antigen or antibody to an immune reaction, separating the labelled antigen or antibody from the labelled antigen-antibody reaction product, bringing either the labelled antigen or antibody or the labelled antigen-antibody reaction product into contact with silver halide, exposing the same to light having a wavelength which the spectral sensitizer absorbs, developing the exposed silver halide and measuring the resulting optical density has been proposed in U.S. application Ser. No. 126,920 filed Mar. 3, 1980, now U.S. Pat. No. 4,337,063, by the present inventors; according to this method, spectral sensitizers for photographic use are employed as labelling substances.

SUMMARY OF THE INVENTION

In this invention, spectral sensitizers are employed as labelling substances; however, this invention is characterized by the fact that a cyanine dye or merocyanine dye comprising a carboxy-containing substituent at a specific position is employed as the spectral sensitizer.

In more detail, this invention is directed to a method for immunochemically measuring an antigen or antibody which comprises:

Labelling an antigen or antibody with a cyanine dye or merocyanine dye comprising a carboxy-containing substituent at a specific position as a labelling substance;

subjecting the thus labelled antigen or antibody to an immune reaction;

bringing either the reaction product (B) or unreacted material (F) into contact with silver halide simultaneously with or after B/F separation;

exposing either B or F to light having a wavelength which the corresponding dye absorbs;

developing the exposed silver halide; and measuring the resulting optical density.

The term "B" and "F" refer to bound antigen or antibody and free antibody or antigen, respectively.

PREFERRED EMBODIMENTS OF THE INVENTION

The cyanine dye employed in accordance with this invention comprises a carboxy-containing substituent bound to an atom other than the nitrogen atom in the cyanine color-forming moiety of the terminal heterocyclic nucleus of the cyanine dye, and is represented by formula (A):

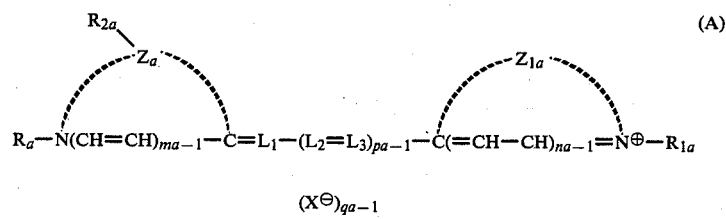

wherein ma and na each represents 1 or 2 and may be the same or different; pa represents 2 or 3; qa represents 1 or 2; L, $L_1$ and $L_2$, which each may be the same or different represents a methine group optionally substituted with a lower alkyl group, an aryl group or a halogen atom; $Z_a$ and $Z_{1a}$, which may be the same or different, each represents the non-metallic atomic group necessary to complete a 5- or 6-membered nitrogen-containing heterocyclic nucleus; X represents an inorganic or organic anion; $R_a$ and $R_{1a}$, which may be the same or different, each represents an alkyl group having 1 to 18 carbon atoms, preferably 1 to 7 carbon atoms, optionally substituted with an aromatic group, an OH group, a sulfo group, etc.; and the cyanine dye forms a betaine type structure when qa is 1; $R_{2a}$ is a substituent on $Z_a$ and represents the carboxy-containing substituent of formula (I):

$$-P_i-Q_{aj}-COOH \quad (I)$$

wherein P represents

—CO—, —O— or —S—, where $R_4$ is a hydrogen atom, an alkyl group having 1 to 8 carbon atoms or a substituted alkyl group, $Q_a$ represents an alkylene group, a substituted alkylene group, an arylene group, a substituted arylene, an aralkylene group, an alkarylene group, a dipeptide residue or a tripeptide residue, 1 and I each is 2 or 4, and 6 and j may be the same or different.

Examples of nitrogen-containing heterocyclic nucleus represented by $Z_a$ and $Z_{1a}$ include thiazole, 4-methylthiazole, 4-phenylthiazole, 4,5-dimethylthiazole, 4,5-diphenylthiazole, benzothiazole, 4-chlorobenzothiazole, 5-chlorobenzothiazole, 6-chlorobenzothiazole, 7-chlorobenzothiazole, 5-nitrobenzothiazole, 6-nitrobenzothiazole, 4-methylbenzothiazole, 5-methylbenzothiazole, 6-methylbenzothiazole, 5-bromobenzothiazole, 6-bromobenzothiazole, 5-iodobenzothiazole, 5-phenylbenzothiazole, 5-methoxybenzothiazole, 6-methoxybenzothiazole, 5-ethoxybenzothiazole, 5-ethoxycarbonylbenzothiazole, 5-phenethylbenzothiazole, 5-fluorobenzothiazole, 5-chloro-6-nitrobenzothiazole, 5-trifluoromethylbenzothiazole, 5,6-dimethylbenzothiazole, 5-hydroxy-6-methylbenzothiazole, tetrahydrobenzothiazole, 4-phenylbenzothiazole, 5-phenylbenzothiazole, naphtho(2,1-d)thiazole, naphtho(2,3-d)thiazole, 5-methoxynaphtho(1,2-d)thiazole, 7-ethoxynaphtho(2,1-d)thiazole, 8-methoxynaphtho(2,1-d)thiazole, oxazole, 4-methyloxazole, 4-nitrooxazole, 5-methyloxazole, 4-phenyloxazole, 4,5-diphenyloxazole, 4-ethyloxazole, benzoxazole, 5-chlorobenzoxazole, 5-methylbenzoxazole, 5-bromobenzoxazole, 5-fluorobenzoxazole, 5-phenylbenzoxazole, 5-methoxybenzoxazole, 5-nitrobenzoxazole, 5-trifluorobenzoxazole, 5-hydroxybenzoxazole, 6-methylbenzoxazole, 6-chlorobenzoxazole, 6-nitrobenzoxazole, 6-methoxybenxoxazole, 6-hydroxybenzoxazole, 5,6-dimethylbenzoxazole, 4,6-dimethylbenzoxazole, 5-ethoxybenzoxazole, naphtho(2,1-d)oxazole, naphtho(1,2-d)oxazole, naphtho(2,3-d)oxazole, 5-nitronaphtho(2,1-d)oxazole, 4-methylselenazole, 4-nitroselenazole, 4-nitroselenazole, 4-phenylselenazole, benzoselenazole, 5-chlorobenzoselenazole, 5-nitrobenzoselenazole, 5-methoxybenzoselenazole, 5-methoxybenzoselenazole, 5-hydroxybenzoselenazole, 6-nitrobenzoselenazole, 5-chloro-6-nitrobenzoselenazole, naphtho(2,1-d)selenazole, naphtho(1,2-d)selenazole, a 1-alkylimidazole, a 1-alkyl-4-phenylimidazole, a 1-alkylbenzimidazole, a 1-alkyl-5-chlorobenzimidazole, a 1-alkyl-5,6-dichlorobenzimidazole, a 1-alkyl-5-methoxybenzimidazole, a 1-alkyl-5-cyanobenzimidazole, a 1-alkyl-5-fluorobenzimidazole, a 1-alkyl-5-trifluoromethylbenzimidazole, a 1-alkylnaphthao(1,2-d)imidazole, a 1-aryl-5-chlorobenzimidazole, a 1-arylimidazole, a 1-arylbenzimidazole, a 1-aryl-5-chlorobenzimidazole, a 1-aryl-5,6-dichlorobenzimidazole, a 1-aryl-5-methoxybenzimidazole, a 1-aryl-5-cyanobenzimidazole, a 1-arylnaphtho(1,2-d)imidazole; wherein the alkyl group represents methyl, ethyl, propyl, isopropyl, butyl, a 2-hydroxyalkyl group or a 3-hydroxypropyl, and the aryl represents a phenyl group, e.g., chlorine-substituted phenyl, methyl-substituted phenyl or methoxy-substituted phenyl. Examples of the nitrogen-containing heterocyclic nuclei represented by $Z_a$ and $Z_{1a}$ further include 2-pyridine, 4-pyridine, 5-methyl-2-pyridine, 3-methyl-4-pyridine, 2-quinoline, 3-methyl-2-quinoline, 5-ethyl-2-quinoline, 6-methyl-2-quinoline, 6-nitro-2-quinoline, 8-fluoro-2-quinoline, 6-methoxy-2-quinoline, 6-nitro-2-quinoline, 8-chloro-2-quinoline, 4-quinoline, 6-ethoxy-4-quinoline, 6-nitro-4-quinoline, 8-chloro-4-quinoline, 8-fluoro-4-quinoline, 8-methyl-4-quinoline, and 8-methoxy-4-quinoline.

Preferred examples of $R_a$ or $R_{1a}$ include methyl, ethyl, propyl, butyl, hexyl, benzyl, β-phenylethyl, 2-hydroxyethyl, 2-methoxyethyl, 2-(2-methoxyethoxy)ethyl, 2-sulfoethyl, 3-sulfopropyl, 3-sulfobutyl, 2-(pyrrolidin-2-on-1-yl)ethyl and tetrahydrofurfuryl; in addition, such examples further include 2-acetoxyethyl, carbomethoxymethyl, 2-methanesulfonylaminoethyl, etc.

Examples of inorganic or organic anions for X include chloride, bromide, iodide, p-toluenesulfonate, p-nitrobenzenesulfonate, methanesulfonate, methylsulfate, ethylsulfate, perchlorate, etc.

Examples of $Q_a$ in the carboxy-containing substituent of formula (I) as substituent $R_{2a}$ on $Z_a$ include substituted alkylene,

wherein $R_5$ represents methyl, ethyl, propyl, isopropyl, isobutyl, tert-butyl, hydroxymethyl, 1-hydroxyethyl, mercaptomethyl, 2-methylthioethyl, benzyl, p-hydroxybenzyl, 3-indolylmethyl, etc., and phenylene. Representative examples thereof include:

—COOH, —CH$_2$COOH, —(CH$_2$)$_2$COOH,

—NHCOCH$_2$CH$_2$COOH, —NHCOCH$_2$CH$_2$CH$_2$COOH,

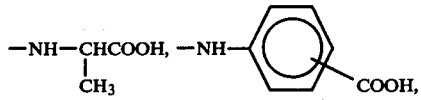

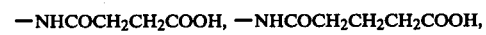

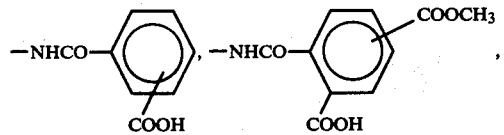

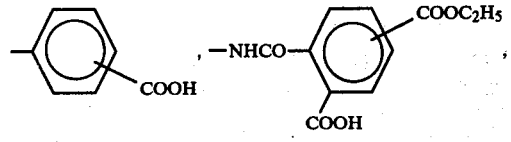

—CONHCH$_2$COOH, —CH$_2$— 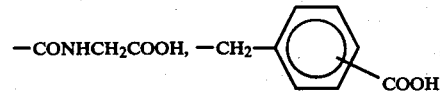

—CONHCHCOOH, —CONHCH$_2$CH$_2$COOH,
     |
     CH$_3$

—CONH—CH—COOH, 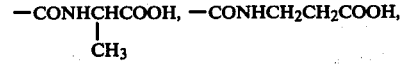

—CO(NHCH$_2$CO)$_2$OH  —CONHCH$_2$CH$_2$COOH,

—CO(NHCH$_2$CO)$_2$OH, —CO(NHCH$_2$)$_3$OH,

—CH$_2$C$_6$H$_4$COOH, —C$_6$H$_4$CH$_2$CH$_2$COOH, and

—CH$_2$CH$_2$C$_6$H$_4$COOH.

In formula (A) above and formula (B) below, unless otherwise indicated, an alkyl group (including a substituent, if any, and also including the alkyl moiety present in an alkoxy group, a dialkylamino group, etc.) generally possesses 1 to 12 carbon atoms, preferably 1 to 5 carbon atoms in total and an aryl group (including a substituent, if any, and also including the aryl moiety present in an aryloxy group, a diarylamino group, etc.) generally possesses 6 to 18 carbon atoms, preferably 6 to 11 carbon atoms.

The merocyanine dye which is employed as a labelling substance in this invention comprises a carboxy-containing substituent on the heterocyclic nuclei thereof, either the basic nucleus or the acidic nucleus of the merocyanine dye, and is represented by formula (B):

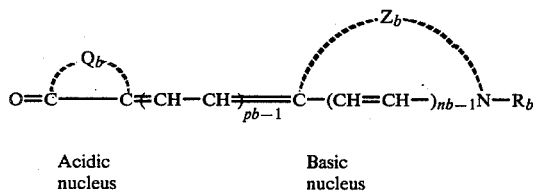

$$O=C\underset{\underset{\text{Acidic nucleus}}{}}{\overset{Q_b}{\frown}}C \doublebond CH-CH\overset{}{\underset{pb-1}{=}}C-(CH=CH-)_{nb-1}\underset{\underset{\text{Basic nucleus}}{}}{\overset{Z_b}{\frown}}N-R_b \quad (B)$$

wherein pb represents an integer of 2 or 3; nb represents an integer of 1 or 2; Zb represents the non-metallic atomic group necessary to complete a 5- or 6-membered nitrogen containing heterocyclic nucleus (basic nucleus); $Q_b$ represents the non-metallic atomic group necessary to complete a 5- or 6-membered nitrogen-containing heterocyclic nucleus (acidic nucleus), wherein the hetero atom(s) is/are exemplified by nitrogen, sulfur, selenium and oxygen; $R_b$ is an alkyl group having 1 to 18 carbon atoms, preferably 1 to 7 carbon atoms, which may be substituted with an aromatic group, an OH group, a sulfo group, etc. In formula (II), the carboxy-containing substituent is bound to the nitrogen-containing heterocyclic nucleus.

The terms "acidic nucleus" and "basic nucleus" used herein are defined in *The Theory of the Photographic Process* (4th ed.), edited by T. H. James, Chapter 8, published by Macmillan Co., Ltd. (1977).

Preferred examples of the basic nucleus Zb include thiazole, 4-methylthiazole, 4-phenylthiazole, 4,5-dimethylthiazole, 4,5-diphenylthiazole, benzothiazole, 4-chlorobenzothiazole, 5-chlorobenzothiazole, 6-chlorobenzothiazole, 7-chlorobenzothiazole, 5-nitrobenzothiazole, 6-nitrobenzothiazole, 4-methylbenzothiazole, 5-methylbenzothiazole, 6-methylbenzothiazole, 5-bromobenzothiazole, 6-bromobenzothiazole, 5-iodobenzothiazole, 5-phenylbenzothiazole, 5-methoxybenzothiazole, 6-methoxybenzothiazole, 5-ethoxybenzothiazole, 5-ethoxycarbonylbenzothiazole, 5-phenethylbenzothiazole, 5-fluorobenzothiazole, 5-chloro-6-nitrobenzothiazole, 5-trifluoromethylbenzothiazole, 5,6-dimethylbenzothiazole, 5-hydroxy-6-methylbenzothiazole, tetrahydrobenzothiazole, 4-phenylbenzothiazole, 5-phenylbenzothiazole, naphtho[2,1-d]thiazole, naphtho[1,2-d]thiazole, naphtho[2,3-d]thiazole, 5-methoxynaphtho[1,2-d]thiazole, 7-ethoxynaphtho[2,1-d]thiazole, 8-methoxynaphtho[2,1-d]thiazole, 5-methoxynaphtho[2,3-d]thiazole, oxazole, 4-methyloxazole, 4-nitrooxazole, 5-methyloxazole, 4-phenyloxazole, 4,5-diphenyloxazole, 4-ethyloxazole, benzoxazole, 4-ethyloxazole, benzoxazole, 5-chlorobenzoxazole, 5-methylbenzoxazole, 5-bromobenzoxazole, 5-fluorobenzoxazole, 5-phenylbenzoxazole, 5-methoxybenzoxazole, 5-nitrobenzoxazole, 5-trifluorobenzoxazole, 5-hydroxybenzoxazole, 6-methylbenzoxazole, 6-chlorobenzoxazole, 6-nitrobenzoxazole, 6-methoxybenzoxazole, 6-hydroxybenzoxazole, 5,6-dimethylbenzoxazole, 4,6-dimethylbenzoxazole, 5-ethoxybenzoxazole, naphtho[2,1-d]oxazole, naphtho[1,2-d]oxazole, naphtho[2,3-d]oxazole, 5-nitronaphtho[2,1-d]oxazole, 4-methylselenazole, 4-nitroselenazole, 4-phenylselenazole, benzoselenazole, 5-chlorobenzoselenazole, 5-nitrobenzoselenazole, 5-methoxybenzoselenazole, 5-hydroxybenzoselenazole, 6-nitrobenzoselenazole, 5-chloro-6-nitrobenzoselenazole, naphtho[2,1-d]selenazole, naphtho[1,2-d]selenazole, a 1-alkylimidazole, a 1-alkyl-4-phenylimidazole, a 1-alkylbenzimidazole, a 1-alkyl-5-chlorobenzimidazole, a 1-alkyl-5,6-dichlorobenzimidazole, a 1-alkyl-5-methoxybenzimidazole, a 1-alkyl-5-cyanobenzimidazole, a 1-alkyl-5-fluorobenzimidazole, a 1-alkyl-5-trifluoromethylbenzimidazole, a 1-alkylnaphtho(1,2-d)imidazole, a 1-aryl-5,6-dichlorobenzimidazole, a 1-aryl-5-chlorobenzimidazole, a 1-arylimidazole, a 1-arylbenzimidazole, a 1-aryl-5-chlorobenzimidazole, a 1-aryl-5,6-dichlorobenzimidazole, a 1-aryl-5-methoxybenzimidazole, a 1-aryl-5-cyanobenzimidazole, a 1-arylnaphtho(1,2-d)imidazole, etc.; wherein the alkyl group is methyl, ethyl, propyl, isopropyl, butyl, a 2-hydroxyalkyl, 3-hydroxypropyl, etc., and the aryl group is phenyl, halogen, a substituted phenyl, a methyl-substituted phenyl or a methoxy-substituted phenyl. Examples of the basic nucleus further include 2-pyridine, 4-pyridine, 5-methyl-2-pyridine, 3-methyl-4-pyridine, etc., and quinoline nuclei, (e.g., 2-quinoline, 3-methyl-2-quinoline, 5-ethyl-2-quinoline, 6-methyl-2-quinoline, 6-nitro-2-quinoline, 8-fluoro-2-quinoline, 6-methoxy-2-quinoline, 6-hydroxy-2-quinoline, 8-chloro-2-quinoline, 4-quinoline, 6-ethoxy-4-quinoline, 6-nitro-4-quinoline, 8-chloro-4-quinoline, 8-fluoro-4-quinoline, 8-methyl-4-quinoline, 8-methoxy-4-quinoline, etc.).

Examples of the groups represented by $R_b$ include methyl, ethyl, propyl, butyl, benzyl, β-phenethyl, 2-hydroxyethyl, 2-methoxyethyl, 2-(2-methoxyethoxy)ethyl, carboxymethyl, 2-carboxyethyl, 3-carboxypropyl, 4-carboxybutyl, 2-sulfoethyl, 3-sulfopropyl, 3-sulfobutyl, 4-sulfobutyl, 2-(pyrrolidin-2-on-1-yl)ethyl, tetrahydrofurfuryl, 2-acetoxyethyl, carbomethoxymethyl, 2-methanesulfonylaminoethyl, etc.

Representative examples of the carboxy-containing group which fall within formula (I) include:

those where carboxy-containing substituents of the merocyanine dye (B) are represented by formula (I) described above, and specific examples thereof are also described above.

In merocyanine dye (B), it is particularly preferred that the carboxy-containing substituent be substituted on the acidic nucleus thereof.

Examples of the nitrogen-containing heterocyclic nuclei containing $Q_b$(acidic nuclei) include a pyrazolin-5-one nucleus, a barbituric acid nucleus or a 2-thiobarbituruc acid nucleus, a rhodanine nucleus, a 2-thio-2,4-oxazolidinedione nucleus, a thiazolidinedione nucleus, an isoxazolone nucleus, 2,4-imidazolidinedione (hydantoin) nucleus, a 2-thio-2,4-imidazolidinedione nucleus, i.e., a 2-thiohydantoin nucleus, a 2-imidazolin-5-one nucleus, etc.

Typical examples include a 3-methyl-1-(4-carboxyphenyl)-2-pyrazolin-5-one nucleus, a 1-(4-carboxyphenyl)-2-pyrazolin-5-one nucleus, a 1-(5-carboxybenzothiazol-2-yl)-3-methyl-2-pyrazolin-5-one nucleus, a 1-(4-carboxyphenyl- or 1-carboxymethyl containing barbituric acid nucleus or thiobarbituric acid nucleus, etc., a 3-carboxymethylrhodanine nucleus, a 3-(2-carboxyethyl)rhadanine nucleus, 3-(4-carboxybutyl)rhodanine nucleus, a 3-(4-carboxyphenyl)rhodanine nucleus, 3-(3-carboxypropyl)-2-thio-2,4-oxazolidinedione nucleus, a 3-(4-carboxyphenyl)-2,4-thiazolidinedione nucleus, a 3-(4carboxyphenyl)-4-thiazolidinone nucleus, a 3-(4-carboxyphenyl)-5-(4H)isoxazolone nucleus, a 3-(2- carboxyethyl)-5-(4H)-isoxazolone nucleus, a 3-carboxymethyl-2,4-imidazolidinedione nucleus, a 3-(2-carboxyethyl)-2,4-imidazolidinedione nucleus, 3-(4-carboxyphenyl)-2,4-imidazolidinedione nucleus, a 3-carboxymethyl-2-thio-2,4-imidazolidinedione nucleus, a 3-(2-carboxyethyl)-2-thio-2,4-imidazolidinedione nucleus, a 3-(4-carboxyphenyl)-2-thio-2,4-imidazolidinedione nucleus, a 3-(4-carboxyphenyl)-1-ethyl-2-thio-2,4-imidazolidinedione nucleus, a 2-carboxymethyl-2-imidazolin-5-one nucleus, etc.

Of these nuclei, particularly preferred examples are a barbituric acid nucleus or thiobarbituric acid nucleus containing a 1-(4-carboxyphenyl) or 1-carboxymethyl group, a 3-carboxymethylrhodanine nucleus, a 3-(2-carboxyethyl)rhodanine nucleus, a 3-(3-carboxypropyl)rhodanine nucleus, a 3-(4-carboxybutyl)rhodanine nucleus, a 3-(4-carboxyphenyl)rhodanine nucleus, a 3-(3 carboxypropyl)-2-thio-2,4-oxazolidinedione nucleus, a 2-thiohydantoin nucleus, a 3-carboxymethyl-2-thio-2,4-imidazolidinedione nucleus, a 3-(2-carboxyethyl)-2-thio-2,4-imidazolidinedione nucleus, a 3-(4-carboxyphenyl)-2-thio-2,4-imidazolidinedione nucleus, a 3-(2-carboxyethyl)- and 2 3-(4-carboxyphenyl)-1-ethyl-2-thio-2,4-imidazolidinedione nucleus.

Specific examples of the spectral sensitizers which are employed as labelling substances in this invention are as follows.

A. Cyanine dyes

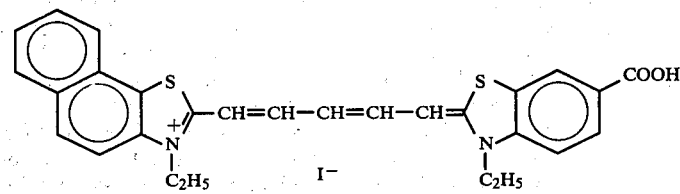

(A-1)

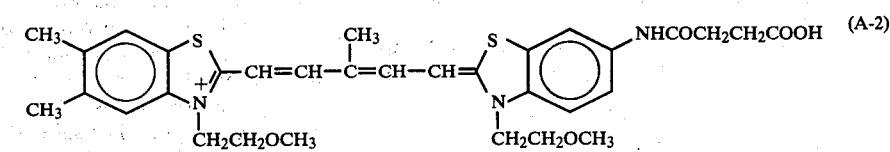

(A-2)

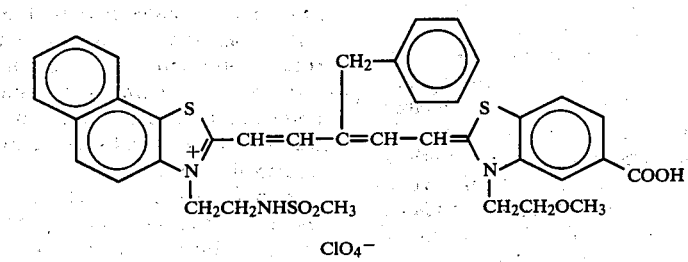

(A-3)

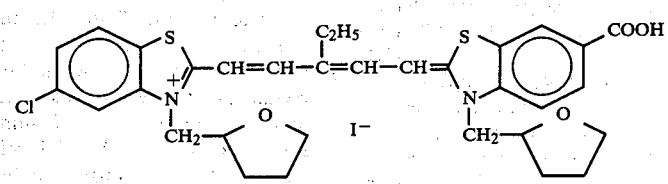

(A-4)

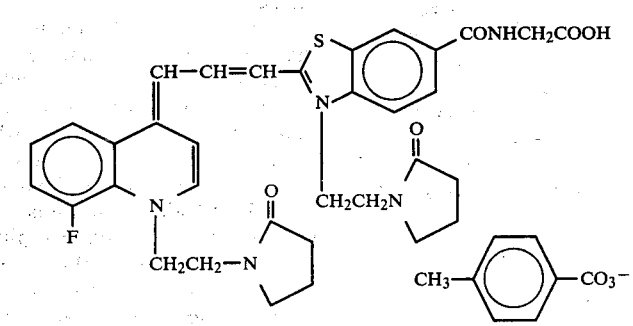

(A-5)

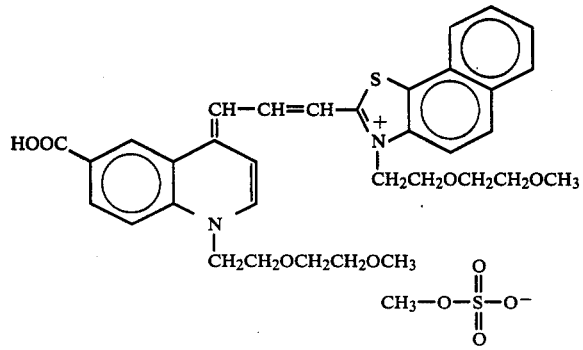
(A-6)
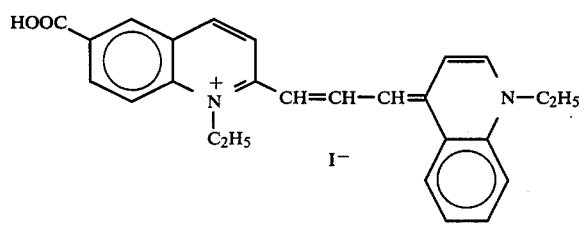
(A-7)
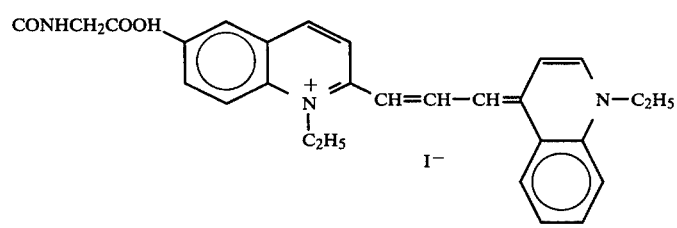
(A-8)
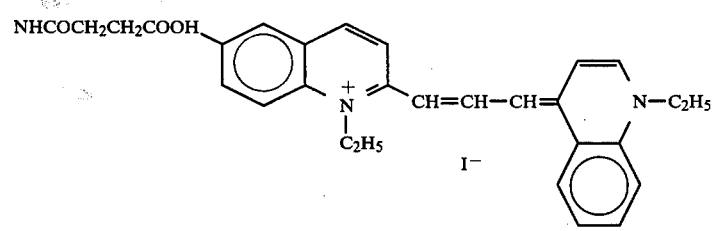
(A-9)
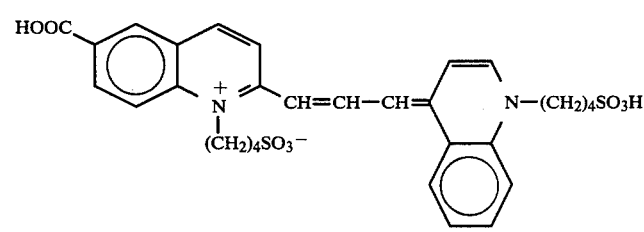
(A-10)
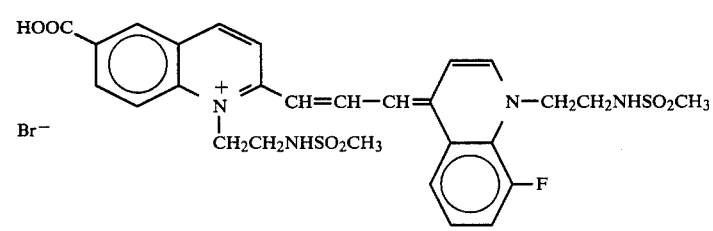
(A-11)

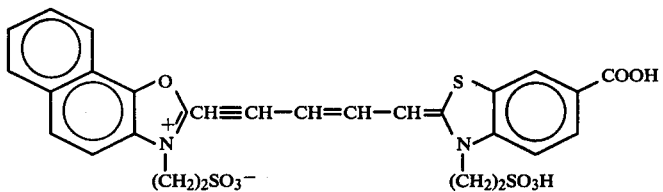
(A-12)
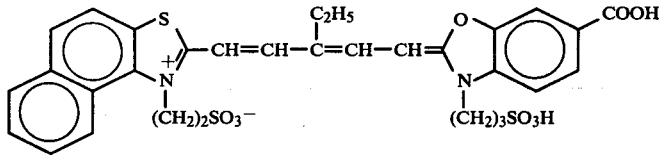
(A-13)
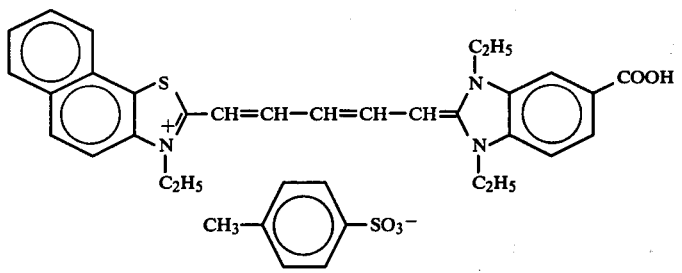
(A-14)
B. Merocyanine Dyes
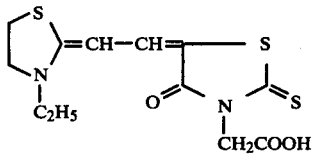
(B-1)
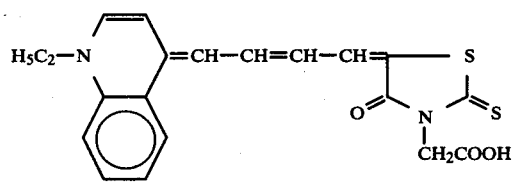
(B-2)
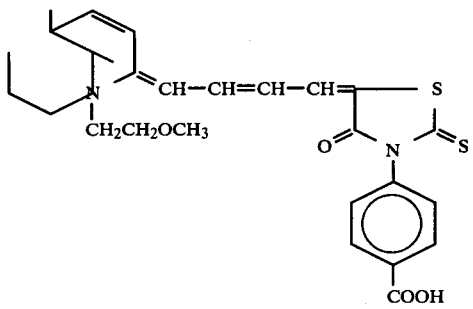
(B-3)

-continued
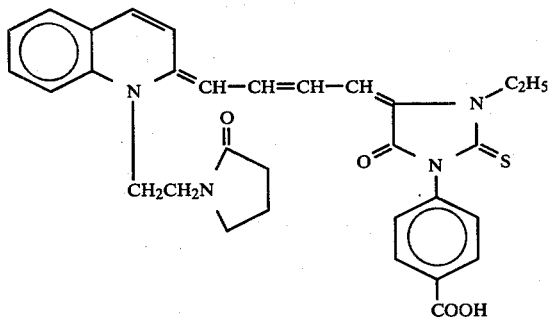 (B-4)
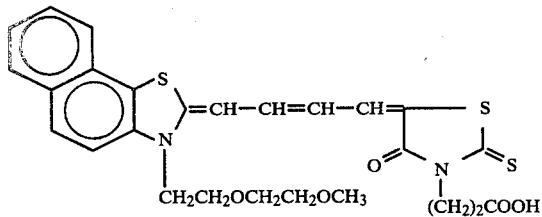 (B-5)
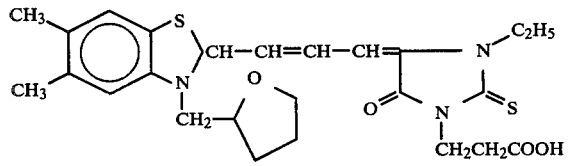 (B-6)
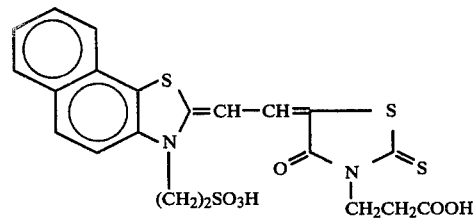 (B-7)
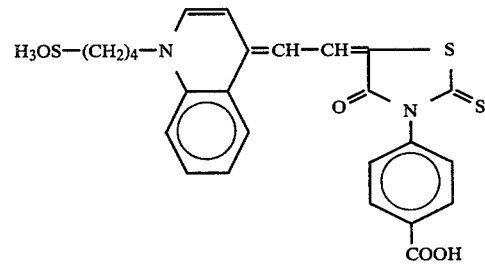 (B-8)
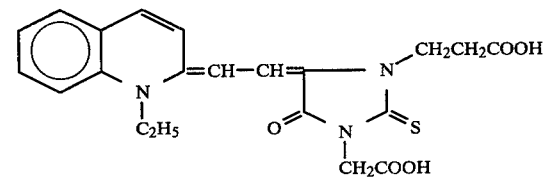 (B-9)

-continued
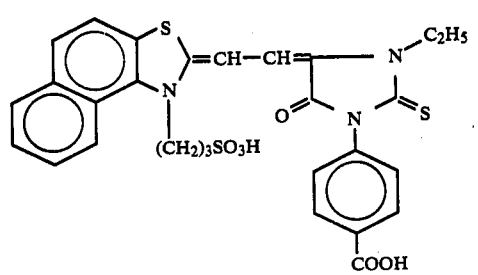 (B-10)
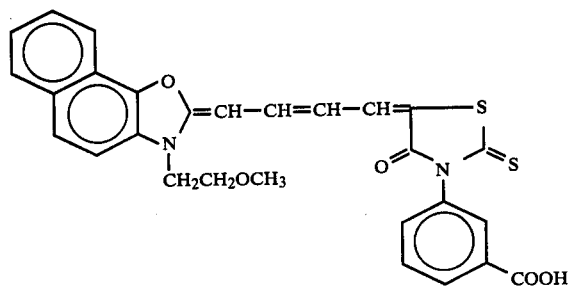 (B-11)
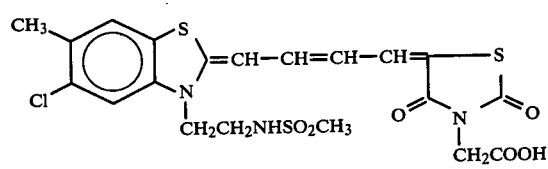 (B-12)
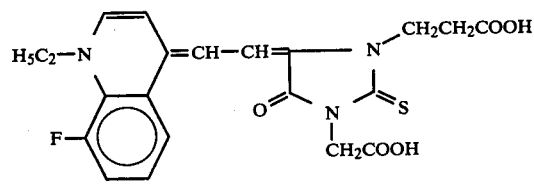 (B-13)
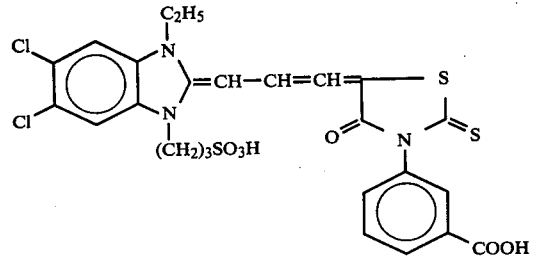 (B-14)
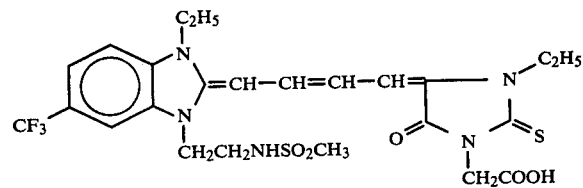 (B-15)
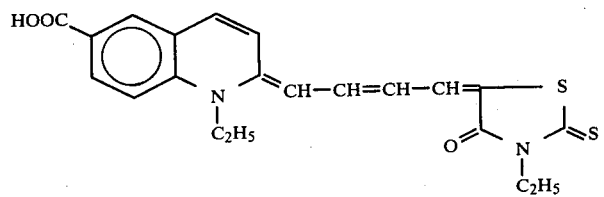 (B-16)

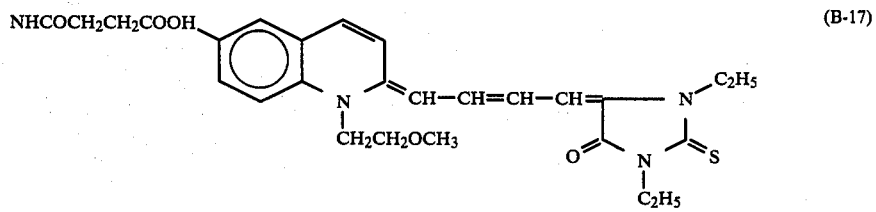
(B-17)

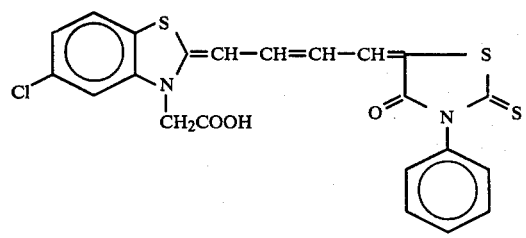
(B-18)

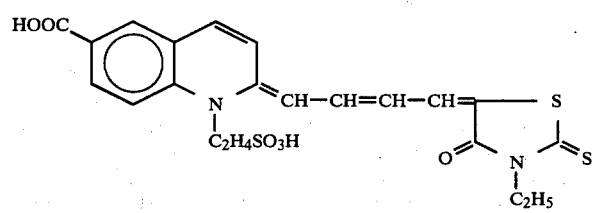
(B-19)

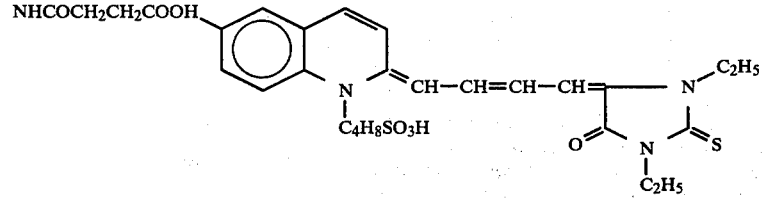
(B-20)

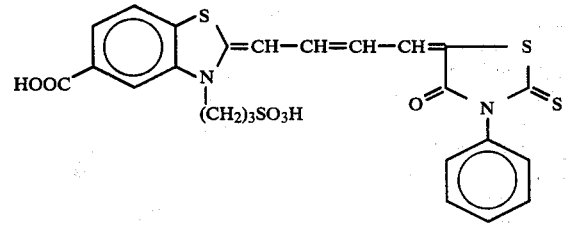
(B-21)

These compounds, including syntheses thereof, are described in F. M. Hamer, CYANINE DYES AND RELATED COMPOUNDS, published by Interscience Publishers (1964).

The labelling substance employed in this invention contains a carboxy-containing substituent of formula (I) and labelling can be effected by applying peptide bond-forming reactions utilized in peptide chemistry and protein chemistry to antigens or antibodies.

As exemplary of such peptide bond-forming reactions, there are the methods described below.

(1) Activating a terminal carbon atom

An acid chloride method (—COCl), an acid azide method (—CON₃), a mixed anhydride method (MA method) (MA or the like prepared using ethyl chloroformate, isobutyl chloroformate, pivalic acid chloride, isovaleric acid chloride, diphenyl phosphochloride, phosphorous oxychloride or sulfuric anhydride), an activated ester method (p-nitrophenyl ester, trichlorophenyl ester, pentachlorophenyl ester, cyanomethyl ester, thioglycolic acid ester, N-hydroxyphthalimide ester, N-hydroxysuccinimide ester, N-hydroxy-5-norbornene-2,3-dicarboxyimide ester, N-hydroxypiperidine ester, 8-hydroxyquinoline ester, 2-hydroxyphenyl ester, 2-hydroxy-4,5-dichlorophenyl ester, 2-hydroxypyridine ester, 2-pyridylthiol ester, etc.), a symmetric acid anhydride method, an ethoxyacetylene method, an enamine method, etc.

(2) Coupling

An N,N'-dicyclohexylcarbodiimide (DCC) method, a DCC-N-hydroxysuccinimide method, a DCC-1-hydroxybenzotriazole method, a carbonyl diimidazole method, an N-ethyl-5-isoxazolium-3'-sulfonic acid salt (Reagent "K") method, a 2-ethyl-7-oxybenzisoxazolium trifluoroborate method, a 1-ethoxycarbonyl-2-ethoxy-1,2-dihydroquinone method.

(3) Activating the terminal nitrogen

An isocyanate method, a phosphazo method, a phosphite ester method.

The merocyanine dyes and cyanine dyes shown by formulae (A) and (B) are excellent as labelling substances for this invention, for example, in solubility, reaction yield, etc.

Groups which are reactive with the aforesaid functional groups of antigens or antibodies and methods for reacting the same are described in detail, in, e.g., *Lectures on Experimental Biochemistry*, vol. 1 subtitled "Chemistry of Proteins", ibid., vol. 2, subtitled "Chemistry of Nucleic Acids", ibid., vol. 3 subtitled "Chemistry of Lipids" and ibid., vol. 4, subtitled "Chemistry of Sugars", all edited by the Biochemical Association, Japan, published by Tokyo Kagaku Dojin (1977); Izumiya, PEPTIDE GOSEI (Peptide Synthesis), Greenstein et al. CHEMISTRY OF THE AMINO ACIDS, vols. I–III (1961), John-Wiley & Sons Inc., New York. One skilled in the art can easily perform such reactions for forming the linking from knowledge in the art and these publications.

Examples of compounds containing groups which react with the aforesaid functional groups further include, e.g., activated esters, activated halogens, aldehydes, activated vinyl esters, activated halogens, aldehydes, activated vinyl compounds, acid anhydrides, acid halides, thioisocyanates, isocyanates, carboxylic acids, amides, alkyl halides, nitrophenyl halides, etc. Accordingly, these functional groups can originally be present in the spectral sensitizer or can be introduced as a result of the reaction of a compound having a bifunctional group and the spectral sensitizer.

Reaction conditions for labelling vary depending upon the kind of the antigen or antibody, the kind of spectral sensitizer, etc., and conditions are selected so as to not damage the biological activity of the antigen or antibody to be labelled. Accordingly, the reaction temperature is generally chosen from the range of from 40° to 60° C., preferably $-20°$ to 40° C.; and the reaction time from the range of from 10 mins. to 16 hrs. The reaction pressure is preferably atmospheric pressure, but can suitably chosen from the range of 1 to 20 atms. It is advantageous that water or a pH buffer solution be used as a solvent for the labelling. Organic solvents such as DMF (dimethylformamide), methylene chloride, etc. can also be employed. These reaction conditions are common to reaction conditions which are generally applicable to modification of proteins or enzymes and details are described in the publications referred to above.

The amount of spectral sensitizer used for labelling varies depending upon the kind of the aforesaid substances to be labelled, but is generally in a molar ratio of 1/100 to 100 moles per 1 mole of the antigen or antibody, preferably 1/20 to 20 times, more preferably $\frac{1}{2}$ to 2 times, same basis.

As methods for confirming completion of labelling, methods for measuring spectra such as UV, visible rays, IR, mass and NMR spectra, etc., and a method confirming labelling via disappearance of the terminal group at which the labelling substance is to be introduced, are representative. Simple tests will be enough to confirm completion of labelling. Where it is confirmed utilizing absorption spectrum, following completion of the labelling reaction, an absorption spectrum of a separated and purified product is measured; if the resulting absorption spectrum is consistent with the intrinsic absorption spectrum which a spectral sensitizer possesses, it is confirmed that the labelling reaction be effected. A further method for confirming the labelling being effected is to analyze the presence or absence of the specific terminal groups, e.g., an amino or carboxy group(s). In the case that the spectral sensitizer is introduced at the terminal amino group(s) of the spectral sensitizer, it is confirmed by the analysis of the N-terminal that completion of the labelling reaction has been effected if the corresponding amino acid(s) to an amino group(s) on which labelling is to occur are not detectable. Detailed disclosure on such N terminal analysis is described in, e.g., B. S. Hartley and V. Massey, *Biochim. Biophys. Acta*, 21, 58 (1956) (generally referred to as a Dansyl method in the art), *Archn. Biochem. Biophys.*, 22, 475 (1949) (a PTC (phenol isocyanate) method), F. Sanger, *Biochem. J.*, 39, 507 (1945) (a dinitrofluorobenzene method), etc. In a similar manner, the terminal carboxy group(s) are analyzed to check completion of the labelling reaction, details of which are given in, e.g., S. Akabori, K. Ohno and K. Narita, *Bull. Chem. Soc. Japan*, 25, 214 (1952) (generally referred to as a hydrazine decomposition method in the art), H. Matuo, U. Fujimoto and T. Tatuno, *Biochem. Biophys. Res. Comminication*, 22, 69 (1966) (a tritium marking method), etc. Further, details of these terminal determination methods are also given as a review in S. B. Needleman, PROTEIN SEQUENCE DETERMINATION, published by Springer Verlag (Berlin), 1975.

According to the aforesaid spectral methods, after the labelling reaction is completed, the reaction product is separated and purified; thereafter the spectrum inherent to the labelled reaction product is measured to confirm the completion of labelling. For example, visible absorption spectrum is measured, and if the spectrum is identical with the inherent absorption spectrum of the spectral sensitizer used for the labelling in the visible region, taking into account solvation, association, etc., completion of the labelling is confirmed. As is described above, if the labelling is effected the terminal amino group or carboxy group of the trace component is not detected upon analysis for the terminal group, and the effected labelling is thereby confirmed.

To separate the labelled antigen-antibody reaction product (B) from the labelled free antigen or antibody (F) in method (I) of this invention, various separation techniques conventionally used in the art are employed. Typical examples include liquid chromatography techniques (e.g., gel filtration, ion exchange, partition chromatography, adsorption chromatography including affinity chromatography, microfilter filtration, dialysis, adsorption using cellulose, talc, dextran powder, etc., salting out (separation of precipitated and aggregated matters formed by adding a salt to a system, see, L. Wide and C. A. Gemzell, *Ciba Foundation Colloq. on Endocrinol.*, 14, 296 (1962)), precipitation (separation of crystallized specific protein formed due to difference of dielectric point, etc., which occurs by changing pH, see, G. M. Brodsky and P. H. Forsham, *J. Clin. Invest.*, 39, 1070 (1960)), centrifugation, crystallization, extraction, solid phase separation, etc., can be used. Detailed disclosure of these separation techniques is provided in Kazuo Shizume and Yuichi Kumahara, NEW RADIOIMMUNOASSAY, 1967, published by Asakura Publishing Co., Ltd., Tokyo, DATABOOK OF BIOCHEMISTRY, second separate volume, Chapter 10, edited by the Biochemical Association, Japan, published by Tokyo Kagaku Dojin, 1980, etc.

When dissolving an antigen or antibody labelled with the aforesaid spectral sensitizer in the water-containing medium necessary to carry out the antigen-antibody reaction, if a compound of formula (S) below is also present, the labelled substance is stabilized, whereby the objects of this invention are more effectively accomplished.

$$D_1-A-D_2 \quad (S)$$

wherein $D_1$ and $D_2$ each represents a condensed polycyclic aromatic heterocyclic moiety or an aromatic heterocyclic ring-substituted amino group, which may contain an $-SO_3M$ group, wherein M is a hydrogen atom, an alkali metal or ammonium group, $-A-$ is a divalent aromatic residue which optionally may contain an $-SO_3M$ group where M is as defined above, provided that the $-SO_3M$ group should be present in or substituted on $-A-$ when the $-SO_3M$ group is not present in or substituted on $D_1$ or $D_2$ as the labelled antigen or antibody is highly stable even in an aqueous solution thereof.

In formula (S), examples of the condensed polycyclic aromatic heterocyclic residue represented by $D_1$ and $D_2$ include a 2-benzotriazolyl group, a 2-naphthotriazolyl group, etc.; and examples of the aromatic heterocyclic ring-substituted amino group include a 1,3,5-triazin-2-yl amino group, a 1,3-diamin-2-yl amino group, etc.

Further when a hydrazine compound represented by formula (H):

wherein $R^{1h}$ represents an aryl group or a substituted aryl group, and $R^{2h}$ represents a hydrogen atom, an alkyl group, a substituted alkyl group, an aryl group or a substituted aryl group, is also present during silver halide development in the immunochemical analysis in accordance with this invention, the optical density of the developed silver or colored dye is increased, which is advantageous for measurement. In this case, an agent to intensify density can be incorporated at any step prior to development. In formula (H), an alkyl group generally has 1 to 12 carbon atoms in total, preferably 1 to 5 carbon atoms, and an aryl group generally has 6 to 18 carbon atoms in total, preferably 6 to 11 carbon atoms.

Examples of antigens or antibodies to be labelled in this invention typically include peptide hormones (e.g., insulin, glucagon, parathyroid hormone, carcitonin, erythropoietin, secretin, cholecystokinin, gastrin, angiotensin II, vasopressin, oxytocin, melanocyte-stimulating hormone, adrenocorticotropic hormone, growth hormone, prolactin, luteinizing hormone, follicle-stimulating hormone); non-peptide hormones (e.g., steroid hormones such as glucocorticoid, aldosterone, adrenergic androgen, estrogen, progesterone, testosterone), or other hormones such as thyroid hormones (e.g., thyroxine, triiodothyronine), cortisol, estriol, adrenaline, noradrenaline, melatonine, acetylcholine, enzymes, e.g., lysozyme, $C_1$ esterase, alkali phosphatase, pepsinogen, trypsin, kinase, virus, specific antigens, tumor antigen, α-fetoprotein, serum protein components, e.g., thyroxine-bound globulin, 2-microglobulin, IgG, IgE, IgM, IgA, human lysozyme; drugs (e.g., LSD, etc.); and others (e.g., rheumatoid factor, $B_s$ antigen, $B_s$ antibody, myosin, etc.).

Specific examples of silver halide to be brought into contact with the antigen-antibody reaction product (B) or the unreacted material (F) include silver chloride, silver chlorobromide, silver bromide, silver iodobromide, silver chloroiodobromide, silver chloroiodide, silver iodide, etc.

These silver halides can be emulsion dispersed or suspended in hydrophilic colloid binder solution or can be supported onto a support without any binder.

The amount of silver halide contained in the silver halide layer used for this invention is preferably in the range of from about 0.5 to about 6.0, more preferably about 1.5 to about 4.5, expressed as an optical density after development processing.

Silver halide as disclosed in U.S. Ser. No. 126,920 filed Mar. 3, 1980 can be used as the silver halide in the silver halide layer in this invention.

Silver halide(s) contained in a photographic emulsion used in the present invention can be prepared in a conventional manner, e.g., by a single jet method, a double jet method, or a combination thereof. Useful preparation methods of silver halide emulsions are described in, e.g., Trivelli and Smith, *The Photographic Journal*, vol. 79, pp. 330–338 (1939), C. E. K. Mees, *The Theory of the Photographic Process*, 1966, published by MacMillian, Glafkides, *Photographic Chemistry*, vol. I, pp. 327–336, published by Fountain Press, etc.

The grain size of silver halide(s) in an emulsion(s) employed in this invention is conventional or smaller. It is thus generally preferred that the average grain diameter be 0.04 to 4 microns (e.g., by measurement of number average by the projected area method).

The silver halide emulsions employed in this invention are not chemically ripened but generally are chemically sensitized in a conventional manner, for example, by gold sensitization (as disclosed in U.S. Pat. Nos. 2,540,085, 2,597,876, 2,597,915 and 2,399,083, etc.), by sensitization with metal ions of Group VIII of the Periodic Table, by sulfur sensitization (as disclosed in U.S. Pat. Nos. 1,574,944, 2,278,947, 2,440,206, 2,410,689, 3,189,458 and 3,415,649, etc.), by reduction sensitization (as disclosed in U.S. Pat. Nos. 2,518,698, 2,419,974 and 2,983,610, etc.), or by a combination thereof.

Specific examples of chemical sensitizers include sulfur sensitizers such as allylthio carbamide, thiourea, sodium thiosulfate cystine, etc.; noble metal sensitizers such as potassium chloroaurate, aurous thiosulfate, potassium chloropalladate, etc.; reduction sensitizers such as stannous chloride, phenylhydrazine, reductone, etc.; polyoxyethylene derivatives as described in British Pat. No. 981,470, Japanese Patent Publication 31-6475 and U.S. Pat. No. 2,716,062, etc.; polyoxypropylene derivatives, quaternary ammonium-containing derivatives, etc.

Silver halide emulsions which are employed in this invention can also contain suitable antifoggants and stabilizers. For example, specific antifoggants and stabilizers include thiazolium salts as described in U.S. Pat. Nos. 2,131,038 and 2,694,716, etc.; azaindenes as described in U.S. Pat. Nos. 2,886,437 and 2,444,605, etc.; urazoles as described in U.S. Pat. No. 3,287,135, etc.; sulfocatechols as described in U.S. Pat. No. 3,236,652, etc.; oximes as described in U.S. Pat. Nos. 2,403,927, 3,266,897 and 3,397,987, etc.; nitron; nitroindazoles; polyvalent metal salts as described in U.S. Pat. No. 2,839,405, etc.; thiuronium salts as described in U.S. Pat.

No. 3,220,839, etc.; salts of palladium, platinum and gold as described in U.S. Pat. Nos. 2,566,263 and 2,597,915, etc.

Silver halide emulsions which are used in this invention can also contain, if desired, one or more developing agents (e.g., hydroquinones, catechols, aminophenols, 3-pyrazolidones, ascorbic acid or derivatives thereof, reductones, phenylenediamines, etc.), or combinations of these developing agents. The developing agents can be incorporated into a light sensitive emulsion and/or other suitable layers (e.g., a hydrophilic binder layer) of a photographic element. The developing agents can be incorporated using a suitable solvent or in the form of a dispersion as described in U.S. Pat. No. 2,592,368 or French Pat. No. 1,505,778.

Silver halide emulsions employed in this invention can contain coating aids such as saponin, alkylaryl sulfonates as described in U.S. Pat. No. 3,600,831, etc., amphoteric compounds as described in U.S. Pat. No. 3,133,816, etc., and can further contain antistatic agents, plasticizers, fluorescent whitening agents, developing accelerating agents, air antifogging agents, color toning agents, etc.

As the silver halide emulsion(s) used in this invention, gelatino silver halide emulsions are generally employed but this is not mandatory. For example, instead of gelatin substances that do not adversely affect light sensitive silver halides and are as used for the water absorbing layer can be employed.

Photographic emulsion layers of photographic light sensitive materials used in this invention can contain color image-forming couplers, that is, compounds capable of forming dyes by reaction with the oxidation product of an aromatic amine (normally a primary amine) developing agent (hereafter referred to as a coupler). It is preferred that the coupler be non-diffusible and comprise a hydrophobic group(s) called a ballast group(s) in the molecule thereof. The coupler(s) can be four-equivalent or two-equivalent to silver ions. In addition, the photographic emulsion layers can also contain colored couplers having a color correction effect or couplers releasing a development inhibitor upon development (DIR couplers). The couplers also can be couplers where the product of the coupling reaction is colorless.

To form the silver halide layer of the analysis element used in this invention, conventional techniques in the photographic art can be utilized and details are described in COATING TECHNOLOGY, Yuji Harazaki, published by Asakura Publishing Co., Ltd., 1972, etc. For coating the silver halide emulsion(s), a dip coating method, a roller coating method, a curtain coating method, an extrusion coating method, etc., can be employed.

Other layers such as the water absorbing layer, auxiliary layers, etc., can be provided in a similar manner.

Upon coating, coating aids can be employed. Examples thereof are non-ionic surface active agents such as saponin (steroid type), polyalkylene glycol alkylamines or amides. polyethylene oxide adducts of silicon, glycidol derivatives (e.g., alkenylenesuccinic acid polyglycerides, alkylphenol polyglycerides), aliphatic acid esters of polyvalent alcohols, alkyl esters, urethanes or ethers of sugars, etc.; anionic surface active agents containing acidic groups such as carboxy, sulfo, phospho, sulfato, phosphato, etc., such as triterpenoid type saponin, alkyl carbonates, alkyl sulfonates, alkylbenzene sulfonates, alkylnaphthalene sulfonates, alkyl sulfates, alkyl phosphates, N-acyl-N-alkyltaurines, sulfosuccinates, sulfalkyl polyoxyethylene alkylphenyl ethers, polyoxyethylene alkyl phosphates, etc.; amphoteric surface active agents or phosphates, alkyl betaines, amine imides, amine oxides, etc.; cationic surface active agents such as alkyl amine salts, aliphatic or aromatic quaternary ammonium salts, heterocyclic quaternary ammonium salts such as pyridinium or imidazolium, etc., phosphonium or sulfonium salts containing an aliphatic or heterocyclic ring, etc.

As a support for the analysis element of this invention, flexible supports such as a plastic film, paper, cloth, etc. or rigid supports such as glass, porcelain, metal, etc. Useful examples of flexible supports include a film composed of semisynthetic or synthetic high molecular weight substances such as cellulose nitrate, cellulose acetate, cellulose acetate butyrate, polystyrene, polyvinyl chloride, polyethylene terephthalate, polycarbonate, etc.; a baryta paper layer, a paper sheet having coated thereon or laminated therewith olefinic polymers (e.g., polyethylene, polypropylene, ethylenebutene copolymers, etc.), or the like.

The surfaces of these supports can be subjected to a subbing treatment for improving adhesion to the silver halide layer. Further, a corona discharge, UV radiation or a flame treatment can also be performed, prior to or after the subbing treatment.

In the method of this invention, exposure is performed as follows.

A variety of light sources can be employed for exposing the silver halide brought into contact with the spectral sensitizer. In any case, only light having a wavelength(s) that the spectral sensitizer alone absorbs is employed for exposure, excluding wavelength in the absorption region intrinsic to silver halide. A suitable exposure degree is generally from $10^1$ to $10^{10}$ cms. As light sources, for example, a tungsten lamp, a halogen lamp, a mercury lamp, a xenon lamp, etc. can be employed in combination with a suitable optical filter (e.g., a sharp cut filter manufactured by Fuji Photo Film Co., Ltd.). In addition, a solid laser (e.g., a ruby laser, etc.), a semiconductor laser (e.g., a lead sulfide laser, etc.), a dye laser, a gas laser (e.g., a neon helium laser, an argon laser, etc.) and the like can be advantageously employed.

In this invention, it is preferred that when a transparent film (support) having the emulsion layer thereon is, exposure be performed through the support to the emulsion layer. Upon exposure, it is necessary to employ a light source having overlaid thereon an optical filter to absorb light having wavelengths in the absorption region intrinsic to silver halide, or to use light from which wavelengths in the absorption region intrinsic to silver halide have been filtered out. It is particularly preferred that exposure be performed through a light source having overlaid thereon an optical filter which mainly transmits a light of wavelengths that the spectral sensitizer absorbs.

The emulsion layer exposed as described above is then processed by conventional photographic processing. That is, in the case where the emulsion(s) is coated on a support, development processing techniques as are conventionally used for processing ordinary photographic films or printing paper can be utilized. Further, photographic processing can also be effected by developing, coating or spraying processing solutions on a support having coated thereon the emulsion(s), or dipping the support in processing solutions. Photographic processing can also be performed by incorporating or mixing processing solutions into or with a liquid type emulsion.

When the hydrazine compound shown by formula (H) is present for further enhancing detection sensitivity, development processing is performed in the presence of the hydrazine compound. More specifically, (1) the hydrazine compound is incorporated in at least one hydrophilic colloid layer in the silver halide light sensitive layer-containing analysis element of this invention, or (2) the hydrazine compound is incorporated in a photographic pre-bath prior to development processing, a developer or a buffer solution employed for the immune reaction.

The development processing temperature is generally selected between 18° and 50° C., but can be lower than 18° C. or higher than 50° C. Depending upon the purpose, any development processing forming silver images (black-and-white photographic processing) and color photographic processing comprising development processing to form color images can be used.

The optical density or degree of blackening increases with increase in processing temperature. Accordingly, it is desired that processing be performed at a constant temperature. However, instead of using constant temperature processing, a technique in which the optical density or degree of blackening is not substantially changed by using the aforesaid neutralizing layer and temperature-compensating layer in combination is also effective.

Developing solutions used in the case of black-and-white photographic processing can contain known developing agents. As such developing agents, dihydroxybenzenes (e.g., hydroquinone), 3-pyrazolidones (e.g., 1-phenyl-3-pyrazolidone), aminophenols (e.g., N-methyl-p-aminophenol), 1-phenyl-3-pyrazolines, ascorbic acid, and heterocyclic compounds comprising a condensed 1,2,3,4-tetrahydroquinoline ring and an indolene ring as described in U.S. Pat. No. 4,067,872, etc., can be used singly or as a combination thereof.

The developing agent solutions can generally contain known preservatives, alkali agents, pH buffers, antifogging agents, and, if necessary, dissolution aids, color toning agents, development accelerators, surface active agents, defoaming agents, softening agents, hardening agents, viscosity-imparting agents, etc.

"Lith" type development processing can also be applied to the photographic emulsion of this invention. The term "lith" type development processing refers to development processing which comprises, for the purpose of photographic reproduction of line images or photographic reproduction of half tone images using dots, infectious development at a low concentration of sulfite ions generally using a dihydroxybenzene(s) as a developing agent, the details of which are given in *Photographic Processing Chemistry*, Mason, 163-165 (1966).

As a special aspect of development, a developing method, which comprises treating a light sensitive material in which a developing agent is contained, e.g., in an emulsion layer, in an aqueous alkaline solution can be used. Of such developing agents, a hydrophobic type can be incorporated into an emulsion layer by latex dispersion, as disclosed in *Research Disclosure*, No. 169, RD-16928. Such development processing can also be used in combination with silver salt stabilization, e.g., with a thiocyanate(s).

As fixing solutions, those having compositions conventionally used in photographic processing can be employed, e.g., as fixing agents, organic sulfur compounds such as thiosulfates, thiocyanates and other organic sulfur compounds that are known as having a fixing effect can be employed. The fixing solution can also contain water soluble aluminum salts as a hardening agent.

To form dye images, again conventional methods are used. A nega-posi method (e.g., as described in *Journal of the Society of Motion Picture and Television Engineers*, vol. 61, 667-701 (1953) can also be used; further, a color reversal method which comprises developing with a developer containing a black-and-white developing agent to form negative silver images, then performing at least one overall exposure or other suitable fogging treatment and subsequently color developing to obtain positive color images can also be used; also, a silver dye bleach method which comprises exposing a photographic emulsion layer containing a dye, developing to thereby form silver images, and then bleaching the dye using the silver images as a bleaching catalyst, etc., can be used.

In general, a color developer comprises an aqueous alkaline solution containing a color developing agent. As color developing agents, known primary aromatic amine developing agents, for example, phenylenediamines (e.g., 4-amino-N,N-diethylaniline, 3-methyl-4-amino-N,N-diethylaniline, 4-amino-N-ethyl-N-beta-hydroxyethylaniline, 3-methyl-4-amino-N-ethyl-N-beta-hydroxyethylaniline, 3-methyl-4-amino-N-ethyl-N-beta-methanesulfamidoethylaniline, 4-amino-3-methyl-N-ethyl-N-beta-methoxyethylaniline, etc.) can be used.

In addition, compounds as described in L. F. A. Mason, *Photographic Processing Chemistry*, 226-229, 1966, Focal Press; U.S. Pat. Nos. 2,193,015 and 2,592,364; and Japanese Patent Application Laid Open OPI 48-64933, etc., can be used.

The color developer can also contain a pH buffering agent such as a sulfite, carbonate, borate and phosphate of an alkali metal, a development inhibitor or an antifogging agent such as a bromide, iodide or an organic antifogging agent, etc. The color developer can also contain, if desired or necessary, a hard water softener, a preservative such as hydroxylamine, an organic solvent such as benzyl alcohol or diethylene glycol; a development accelerator such as polyethylene glycol, a quaternary ammonium salt or an amine; a dye forming coupler, a competing coupler, a fogging agent such as sodium borohydride, an auxiliary developing agent such as 1-phenyl-3-pyrazolidone, a viscosity imparting agent, a polycarboxylic acid type chelating agent as described in U.S. Pat. No. 4,083,723, an antioxidant as described in Patent Application (OLS) 2,622,950, etc. Of course, combinations of the above materials can also be used.

The photographic emulsion layer(s) after color development is/are usually subjected to bleaching. Bleaching can be performed with fixing at the same time or separately therefrom. Representative examples of bleaching agents include polyvalent metal compounds of iron (III), cobalt (III), chromium (VI), copper (II), etc., peroxides, quinones, nitroso compounds, etc. For example, ferricyanides, bichromates, inorganic complexes of iron (III) or cobalt (III), aminopolycarboxylic acids such as ethylenediamine tetraacetic acid, nitrilotriacetic acid, 1,3-diamino-2-propanol tetraacetic acid, etc., complexes of organic acides such as citric acid, tartaric acid, maleic acid, etc.; persulfates, permaganates; nitrosophenol, etc., can be employed. Of these, potassium ferricyanide, ethylene diamine tetraacetic acid iron (III) sodium and ethylene diamine tetraacetic acid iron (III) ammonium are particularly useful both in an independent bleaching solution and in a mono bath bleaching-fixing solution.

The bleaching or blix solutions can also contain bleach accelerators as described in U.S. Pat. Nos. 3,042,520 and 3,241,966 and in Japanese Patent Publications 45-8506 and 45-8836, etc., thiol compounds as described in Japanese Patent Application Laid Open (OPI) No. 53-65732 and other various additives.

Processing solutions used in this invention can be liquid compositions containing processing components necessary for the development of silver halide emulsions and the formation of diffusion transfer dye images in which the major portion of the solvent is water and wherein a hydrophilic solvent(s) such as methanol, methyl cellosolve, etc., can also optionally be present in addition to water.

The processing composition should have a pH necessary for development of the emulsion layers and should contain alkali in an amount sufficient to neutralize acids (e.g., hydrogen halides such as hydrogen bromide, carboxylic acids such as acetic acid, etc.) released during various steps for developing and forming dye images. As the alkali, alkali metal or alkaline earth metal salts, e.g., lithium hydroxide, sodium hydroxide, potassium hydroxide, a calcium hydroxide dispersion, hydroxylated tetramethyl ammonium, sodium carbonate, trisodium phosphate, diethyl amine, etc., or other amines are illustrative. Preferably, the alkali is an alkali hydroxide and imparts a pH of at least about 12 at room temperature, more preferably a pH of at least 14.

More preferably, the processing compositions contain hydrophilic polymers such as high molecular weight polyvinyl alcohol, hydroxyethyl cellulose, sodium carboxymethyl cellulose and the like. These polymers impart a viscosity of at least 1 poise at room temperature, preferably several hundred (500 to 600) to 1000 poise to the processing compositions to thereby not only provide uniform development upon processing but also be permit easy transfer of aqueous solvent into the light sensitive element and an image receiving element during processing, where, when the processing compositions are condensed, a non-fluid layer can be formed to assist formation of a film unit which is firmly united after processing. Such a hydrophilic polymer layer prevents, after the formation of a diffusion transfer color image is substantially complete, further transfer of colored component into the image receiving layer to thereby help prevent image changes.

In some cases, it is advantageous that the processing compositions also contain light absorbing substances such as $TiO_2$ or carbon black, pH indicators, or desensitizers as described in U.S. Pat. No. 3,579,333, in order to prevent a silver halide(s) from being fogged by external light. In addition, the processing compositions can also contain development inhibitors such as benzotriazole. The aforesaid processing compositions can be used by encasing the same in a rupturable container as described in U.S. Pat. Nos. 2,543,181, 2,653,732, 2,723,051, 3,056,491, 3,056,492 and 3,152,515, 2,643,886, etc.

According to the method of this invention, detection sensitivity of trace components is high and excellent results with precise accuracy and reproducibility are obtained.

The markers used in the method of this invention do not involve the hazards of radiation as does radioimmunoassay since the markers, i.e., spectral sensitizers, are not radioactive; measurement and inspection can easily be performed by a person not necessarily qualified to deal with radioactive materials.

Hereafter, reactivities of spectral sensitizers used as labelling substances in this invention are examined by reacting the cyanine dyes or merocyanine dye with isobutyl chloroformate or with phenylalanine, in which percentages are all by weight unless otherwise indicated. The "reactivity" is expressed by percentage of the desired peak area to the total peak areas in chromatogram measured at 600 nm.

REFERENCE EXAMPLE 1

A cyanine dye and isobutyl chloroformate were mixed in an equimolar proportion at $-15°$ C. in DMF in the presence of triethyl amine. Five minutes thereafter, TLC (TLC Plate Silica Gel 60 $F_{254}$, manufactured by Merck Inc., solvent for development, $CHCl_3/MeOH = 3/1$ v/v) and the reactivity(%) was measured with a TLC scanner (CS-910, manufactured by Shimazu Seisakusho, wavelength for measurement, 600 nm; reference wavelength, 370 nm). Cyanine dyes of Formulae A-7 and A-9 showed a reactivity of 100% while a dye of Formula A-8 showed 85%.

REFERENCE EXAMPLE 2

Modification of phenylalanine with Dye (B-1)

In 60 ml. of DMF, 3.3 g. (10 mmol) of Dye (B-I) and 1.15 g. (10 mmol) of N-hydroxysuccinic imide were dissolved and the solution was cooled to 5° C.

To the solution, 2.5 g. (12.1 mmols) of N,N'-dicyclohexylanbodiimide was added and the mixture was stirred for 5 hrs. The mixture was then allowed to stand overnight in a refregirator.

N,N'-dicyclohexylurea precipitated was removed by filtration and washed with 100 ml. of DMF. The filtrate and the washed liquid were combined and 30 ml. of water was added thereto. The crystals which precipitated out were removed by filtration. There was thus obtained 2.5 g. the N-hydroxysuccinic acid amide ester (yield 58.8%).

In 15 ml. of DMF, 213.5 mg. (500 $\mu$mol) of this active ester was dissolved and the solution dropwise added to a solution of 200 mg (1.2 mmol) of phenylalanine in 10 ml. of 0.02M tris-hydrochloric acid buffer solution (pH 7.5) at room temperature over approximately one hour. Thereafter, the mixture was stirred for 2 hrs. After standing overnight, the reaction mixture was poured into 100 ml. of water. The crystals which precipitated out were removed by filtration. After washing with water, the crystals were recrystallized from methanol/methylene chloride = 1/1 v/v to obtain 103 mg. (yield, 42.8%) of the desired product; mass spectrum (FD): $m/z = 477$ (M+).

Phenylalanine was modified using Compound (B-2) in a similar manner. The corresponding modified compound was obtained in good yield.

This invention will now be described with reference to the examples below in detail, but is not to be construed as limited thereto.

EXAMPLE 1

In 1 ml. of 4M ("M" means mol/l., hereafter the same) urea, 20 mg (3.5 $\mu$mol) of purified pork insulin (manufactured by Sigma Chemicals Co., Ltd.) was dissolved. To the resulting solution, 8 ml. of N,N-dimethylformamide (DMF herein) was added and the mixture was thoroughly stirred while ice-cooling (0° to 4° C., Liquid A).

Three sets of a solution of 1.31 mg (2.5 μmol) of Dye (A-7) in 1 ml. of DMF were then prepared (total 7.5 μmol) and 1 μl of isobutyl chloroformate and 0.5 μl of triethyl amine (a mixture of 5 μl of triethyl amine and 1 ml. of DMF had previously been cooled and 100 μl therefrom was added; this means the addition of 0.5 μl of triethyl amine) were added to the sets of solutions while cooling at −15° to −20° C., to thereby activate the carboxy group present on Dye (A-7). To the mixture, 0.5 mg. of N-hydroxysuccinimide (100 μl from a mixture of 5 mg. of N-hydroxysuccinimide and 1 ml. of DMF) was further added under cooling to thereby form the activated ester (Liquid B).

Thereafter, Liquid B was added to Liquid A while stirring and ice-cooling over a 5 minutes to cause reaction. After reacting for 30 mins. while ice-cooling and then at room temperature for 30 mins., the reaction mixture was desalted with a Sephadex G-10 column equilibrated with 0.2N ammonia water, and then freeze-dried to obtain dye-labelled insulin; yield 24.6 mg, $\lambda_{max}^{2\%SDS} = 660$ nm (SDS: sodium dodecyl sulfate), $\epsilon_{660\ nm} = 3.2 \times 10^5$ (about 2 mols/mol insulin).

Upon analysis of the amino terminal of the labelled product according to the Dansyl method, glycine and phenylalanine—which were the amino terminals of the pork insulin—were not detected. Further in chromatography using a Sephadex G-50 (1% SDS) column, the labelled insulin showed a single peak and the labelled insulin showed spectral sensitization having a maximum at approximately 685 nm to an AgBrCl emulsion (average grain size, 0.75μ) containing 70 mol% of Br.

EXAMPLE 2

According to a double antibody method in which the pork insulin labelled with Dye (A-7) described in Example 1 was used and, anti-pork insulin guinea pig serum and anti-quinea pig IgG rabbit serum were used as a primary antibody and a secondary antibody, respectively, a calibration curve corresponding to standard insulin having various concentrations (0.2 to 12.8 ng/ml) was prepared as described below.

0.1 ml of standard insulin solutions having various concentrations were separately weighed in small test tubes and, 0.4 ml. of 0.1M tris-hydrochloric acid buffer solution having a pH of 8.5 (Liquid C) containing 0.1M NaCl and 1.0% bovine serum albumin (BSA) was further added to the respective test tubes. Further, 0.1 ml. of a diluted solution of anti-pork insulin quinea pig serum, the titer of which had previously been determined, was added to the test tubes, respectively. Then, 0.1 ml. of the insulin labelled with Dye (A-7) dissolved in and diluted with Liquid C was added. After thoroughly stirring, the mixture was allowed to stand for 16 hrs. at 4° C. Then, 0.1 ml. of a diluted anti-quinea pig IgG rabbit serum solution was added and the mixture was thoroughly stirred to react for 24 hrs. at 4° C. The precipitates formed were removed by centrifugal separation (3000 rpm, 10 mins.), and the respective supernatants were dropped in an amount of 10 μl each to separate areas of 5 mmφ on a film obtained by coating an unexposed AgBrCl emulsion (Br, 70 mol%; average grain size, 0.7 μm) on a TAC ("TAC" cellulose triacetate, hereafter the same) support. After standing for 15 mins at room temperature, exposure was performed for 1 second at 5000 lux through an SC-60 filter, made by Fuji Photo Film Co., Ltd. Thereafter, development was performed with Developer A having the formulation described below at 20° C. for 10 mins. followed by fixing, water washing and drying in a conventional manner.

| Developer A: | |
|---|---|
| Metol | 3.1 g |
| Sodium sulfite | 45 g |
| Hydroquinone | 12 g |
| Anhydrous sodium carbonate | 67.5 g |
| KBr | 1.9 g |
| Water to make | 1 liter |

The resulting black density (optical density) on the film was measured using a photographic densitometer made by Fuji Photo Film Co., Ltd. to obtain the results shown below (dilution of the respective anti-sera and labelled insulin was set to provide a black density of the developed silver between 3.0 and 3.5 at a standard insulin concentration of 12.8 ng/ml).

TABLE 1

| Concentration of Insulin (ng/ml) | Black Density |
|---|---|
| 0 | 0.20* |
| 0.2 | 0.51 |
| 0.4 | 0.90 |
| 0.8 | 1.45 |
| 1.6 | 1.96 |
| 3.2 | 2.50 |
| 6.4 | 3.04 |
| 12.8 | 3.22 |

*background density

EXAMPLE 3

Three samples were formed as follows: in 2 ml. of 2M urea, 50 mg of human lysozyme (purified from urine of patients with leukemia) was dissolved. To the solution, 6 ml. of DMF was further added and the mixture was stirred while ice-cooling (0° to 4° C.). 2 mg. each of Dye (A-9) was weighed in three small test tubes and dissolved by adding 2 ml. of DMF thereto, respectively. To the solutions, 2 μl of isobutyl chloroformate and 1 μl of triethyl amine were added, respectively, while cooling at −15° to −20° C. to thereby activate the carboxy group present on Dye (A-9). Then, the thus activated Dye (A-9) was added to the human lysozyme solutions described above at a 5-minute interval, while ice-cooling and stirring the solutions to thereby cause reaction. After reacting for 30 mins. while ice-cooling, the reaction mixture was desalted with a Sephadex G-10 column equilibrated with 0.2N ammonia water and freeze-dried to obtain the dye labelled-human lysozyme; yield, about 52 mg., $\lambda_{max}^{2\%\ SDS} = 665$ nm, $\epsilon_{660\ nm} = 1.64 \times 10^5$.

On amino terminal analysis of the labelled product according to the Dansyl method, lysine—which was the amino terminal of human lysozyme—was not detected. Further, by chromatography using a Sephadex G-50 column (equilibrated with 1% SDS), the product gave a single peak and in lytic activity using *Micrococcus Lysodeikticus* as a substrate, the product showed almost the same activity as the unmodified enzyme.

The dye (A-9) labelled human lysozyme described in accordance with the procedure above was dissolved in a 0.05M tris-hydrochloric acid buffer solution having a pH of 8.0 and containing 0.1M NaCl and 1% BSA to prepare solutions having concentrations of 1 ng/ml and 0.5 ng/ml. The solutions were spotted on the same film as was used in Example 2 followed by exposure, development and density measurement. The differences in density from a blank (background optical density) were 0.32 and 0.15, respectively.

EXAMPLE 4

Dye-labelled pork insulin was obtained in a manner similar to Example 1 except that Dye (A-2) was employed instead of Dye (A-7); yield 25.3 mg., $\lambda_{max}{}^{2\%\ SDS} = 668$ nm, $\epsilon_{660\ nm} \approx 4.03 \times 10^5$ (2 mols dye/mol insulin).

Using the thus labelled pork insulin, a calibration curve satisfactory for standard insulin could be prepared in accordance with the same double antibody method as described in Example 2.

EXAMPLE 5

Dye-labelled pork insulin was obtained in a manner similar to Example 1 except that Dye (B-2) was employed in place of Dye (A-7) in an amount of 1 mg. (2.75 μmols); yield 21.5 mg., $\lambda_{max}{}^{2\%\ SDS} = 712$ nm, $\epsilon_{712\ nm} \approx 8.9 \times 10^4$ (ca. 2 mols dye/mol insulin).

On amino terminal analysis of the labelled product according to the Dansyl method, neither glycine nor phenylalanine—which were the amino terminals of pork insulin—were detected. Further, in chromatography using a Sephadex G-50 column (equilibrated with 1% SDS), the labelled product showed a single peak and the dye-labelled insulin showed spectral sensitization at a maximum of about 760 nm to a silver chlorobromide emulsion (bromide content, 70 mol%).

EXAMPLE 6

Dye-labelled human lysozyme was obtained in a manner similar to Example 3 except that Dye (B-2) was employed as the labelling substance; yield about 45 mg., $\lambda_{max}{}^{3\%\ SDS} = 712$ nm, $\epsilon_{712\ nm} \approx 4.6 \times 10^4$.

On amino terminal analysis of the labelled product according to the Dansyl method, lysine—which was the amino terminal of hyman lysozyme—was not detected. Further, in chromatography using a Sephadex G-50 column (equilibrated with 1% SDS) the product gave a single peak and in lytic activity using *Micrococcus Lysodeikticus* as a substrate, the product showed almost the same activity as the unmodified enzyme.

Further, this dye-labelled human lysozyme showed spectral sensitization having at a maximum of about 760 nm to an AgBrCl emulsion (Br content, 80 mol%, average grain size 0.8 μm).

EXAMPLE 7

According to a double antibody method in which the pork insulin labelled with Dye (B-2) described in Example 5 above was used, and anti-pork insulin guinea pig serum and anti-guinea pig IgG rabbit serum were used as a primary antibody and a secondary antibody, respectively, a calibration curve corresponding to standard insulin having various concentrations was prepared as described below.

0.1 ml. of standard insulin solutions having various concentrations (0.2 to 12.8 ng/ml) were separately weighed into small test tubes and 0.4 ml. of a 0.1M tris-hydrochloric acid buffer solution having a pH of 8.5 (Liquid C) containing 0.1M NaCl and 1% bovine serum albumin was further added to each test tube. Further, 0.1 ml. each of a diluted solution of anti-pork insulin guinea pig serum, the titer of which had previously been determined, was added to the test tubes, respectively. Then, 0.1 ml. of the insulin labelled with Dye (B-2) dissolved in and diluted with Liquid C was added to each test tube. After thoroughly stirring, the mixture was allowed to stand for 16 hrs. at 4° C. Then, 0.1 ml. of a diluted anti-guinea pig IgG rabbit serum solution was added and the resulting mixture was thoroughly stirred to react for further 24 hrs. at 4° C. The precipitates formed were removed by centrifugal separation (3000 rpm, 10 mins.), and the respective supernatants were dropwise added in 20 μl amounts each to an area of 5 mmφ on a film obtained by coating an unexposed AgBrCl emulsion (Br content, 80 mol%; average grain size, 0.8 μm) on a TAC support.

After standing for 10 mins., exposure (which corresponded to $10^5$ lux $\times 10^{-2}$ sec.) was performed at a distance of 30 cm. through an SC-66 filter, made by Fuji Photo Film Co., Ltd., using a commercially available flash (Guide No. 56). Thereafter, development was performed with Developer A having the same formulation shown in Example 2 at 20° C. for 10 mins. followed by fixing, water washing and drying in a conventional manner.

The resulting black density (optical density) on the film was measured using a photographic densitometer made by Fuji Photo Film Co., Ltd. to obtain the results shown below (dilution of the respective anti-sera and labelled insulin was set to provide a black density of the developed silver between 2.0 and 2.5 at a standard insulin concentration of 12.8 ng/ml).

TABLE 2

| Concentration of Insulin (ng/ml) | Black Density |
| --- | --- |
| 0 | 0.21* |
| 0.2 | 0.45 |
| 0.4 | 0.72 |
| 0.8 | 1.01 |
| 1.6 | 1.35 |
| 3.2 | 1.68 |
| 6.4 | 1.93 |
| 12.8 | 2.23 |

*background density

EXAMPLE 8

Dye-labelled pork insulin was obtained in a manner similar to Example 1 except that Dye (B-5) was employed instead of Dye (A-7) of Example 1. The yield was 19.7 mg.; $_{max}{}^{2\%\ SDS} = 624$ nm, $\epsilon_{624} = 2.00 \times 10^5$ (ca. 2 mols dye/mol insulin).

Next, using the thus obtained labelled pork insulin, a calibration curve satisfactory for standard insulin having various concentrations was obtained according to a double antibody method in a manner similar to Example 8.

While the invention has been described in detail and with reference to specific embodiments thereof, it will be apparent from one skilled in the art that various changes and modifications can be made therein without departing from the spirit and scope thereof.

What is claimed is:

1. A method for immunochemical measurement of an antigen or antibody which comprises labelling an antigen or antibody with a labelling substance,
    said labelling substance being a cyanine or merocyanine dye comprising a carboxy-containing substituent on a heterocyclic nucleus of said dye, wherein said cyanine dye comprises a carboxy-containing substituent bound to an atom other than the nitrogen atom in the cyanine color-forming moiety of the terminal heterocyclic nucleus of said cyanine dye and wherein said merocyanine dye comprises a carboxy-containing substituent on the heterocyclic nucleus of said merocyanine dye.

2. A method for immunochemically measuring an antigen or antibody which comprises:

labelling an antigen or antibody with a cyanine or merocyanine dye comprising a carboxy-containing substituent on a heterocyclic nucleus of said dye, wherein said cyanine dye comprises a carboxy-containing substituent bound to an atom other than the nitrogen atom in the cyanine color-forming moiety of the terminal heterocyclic nucleus of said cyanine dye and wherein said merocyanine dye comprises a carboxy-containing substituent on the heterocyclic nucleus of said merocyanine dye, subjecting the thus obtained dye-labelled antigen or antibody to an immune reaction, bringing either the bound antibody or antigen or the free antigen or antibody into contact with silver halide after or at the same time as B/F separation, exposing the resulting product to light which the corresponding dye absorbs, developing the exposed silver halide, and, measuring the resulting optical density.

3. The method of claim 2 wherein said cyanine dye comprises a carboxy-containing substituent bound to an atom other than the nitrogen atom in the cyanine-color-forming moiety of the terminal heterocyclic nucleus of said dye.

4. The method of claim 1 or 2 wherein said cyanine dye has the formula:

or organic anion; $R_a$ and $R_{1a}$ each represents an unsubstituted or substituted alkyl group; and $R_{2a}$ represents a carboxy-containing substituent.

5. The method of claim 2 wherein said merocyanine dye comprises a carboxy-containing substituent on the heterocyclic nucleus of said merocyanine dye.

6. The method of claim 5 wherein said merocyanine dye is represented by formula:

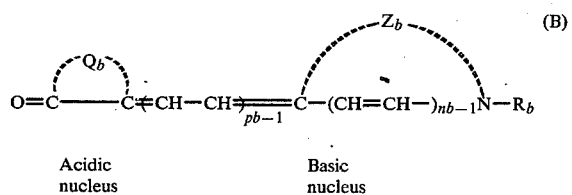

(B)

Acidic nucleus       Basic nucleus wherein pb represents an integer of 2 or 3; nb represents an integer of 1 or 2; $Z_b$ represents the non-metallic atomic group necessary to complete a 5- or 6-membered nitrogen containing heterocyclic basic nucleus; $Q_b$ represents the non-metallic atom group necessary to complete a 5- or 6-membered nitrogen-containing acidic heterocyclic nucleus; and $R_b$ represents an unsubstituted or substituted alkyl group.

7. The method of claim 2, 3, or 4, wherein said carboxy-containing substituent is represented by formula:

$$-P_i-Qa_j-COOH$$

wherein P represents

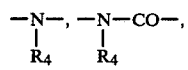

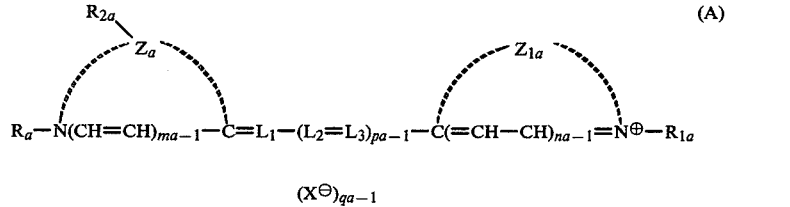

(A)

$(X^\ominus)_{qa-1}$ wherein ma and na each represents 1 or 2 and may be the same or different; pa represents 2 or 3; qa represents 1 or 2; $L_1$, $L_2$ and $L_3$, which each may be the same or different represents a methine group optionally substituted with a lower alkyl group, an aryl group or a halogen atom; $Z_a$ and $Z_{1a}$, which may be the same or different, each represents the non-metallic atomic group necessary to complete a 5- or 6-membered nitrogen-containing heterocyclic nucleus; X represents an inorganic —CO—, —O— or —S— wherein $R_4$ represents a hydrogen atom, an unsubstituted or substituted alkyl group; Qa represents an unsubstituted or substituted alkylene group, an unsubstituted or substituted arylene group, an aralkylene group, an alkarylene group, a dipeptide residue or a tripeptide residue; and i and j each represents 0 or 1 which may be the same or different.

* * * * *